United States Patent
Cattani

[11] Patent Number: 6,090,286
[45] Date of Patent: Jul. 18, 2000

[54] SEPARATOR CENTRIFUGE

[75] Inventor: Ennio Cattani, Parma, Italy

[73] Assignee: Cattani S.p.A., Parma, Italy

[21] Appl. No.: 09/232,217

[22] Filed: Jan. 19, 1999

[30] Foreign Application Priority Data

Jan. 29, 1998 [IT] Italy .................................. MO98A0019

[51] Int. Cl.⁷ .................................................. B01D 21/26
[52] U.S. Cl. ...................... 210/512.1; 209/717; 209/734; 55/459.1; 55/459.5; 433/92
[58] Field of Search ................. 210/512.1, 788; 433/92; 209/717, 718, 719, 734; 55/459.1, 459.4, 459.5

[56] References Cited

U.S. PATENT DOCUMENTS 4,652,363  3/1987  Miller .................................. 210/512.1
5,330,641  7/1994  Cattani .................................. 210/512.1

*Primary Examiner*—David A. Reifsnyder
*Attorney, Agent, or Firm*—Browdy and Neimark, P.L.L.

[57] ABSTRACT

The separator centrifuge for separating solid particles suspended in a fluid comprises a container having an inlet for the fluid and an outlet for the fluid once cleaned of the solid particles, the outlet being situated higher than the inlet. The container has a truncoconical wall converging in a downwards direction, at a smaller end of which is located a discharge which is connected to a chamber for collecting the solid particles. The inlet of the container comprises a plurality of mouths each of which is crossed by a fraction of a total volume of fluid entering the container. The fluid is injected into the container in a direction which has at least one component which is tangential with respect to an axis of the truncoconical wall. The separator is particularly useful for separating solid particles in discharge fluids coming from dental equipment.

10 Claims, 2 Drawing Sheets

U.S. Patent Jul. 18, 2000 Sheet 1 of 2 6,090,286

SEPARATOR CENTRIFUGE

BACKGROUND OF THE INVENTION

The invention relates specifically, though not exclusively, to an application for separating solid particles in discharge fluids coming from dental aspirating equipment.

As is known, dental aspirating equipment removes fluids from the patient's mouth during a dental operation. These fluids comprise a gassy part (generally air), a liquid part (generally water, blood and other liquids used in dental apparatus), as well as a solid part in the FORM of particles (generally comprising dental amalgam). The aspirated fluids contain various polluting substances, such as the solid particles of the amalgam. In dental plants the production of fluids can be rather abundant, though generally discontinuously produced. These fluids, before being discharged into the sewers, must be cleaned of these polluting particles. Thus a possible use of the invention is to liberate the fluids aspirated from these polluting substances.

Separator centrifuges are used for the above operation, which separate the fluids by exploiting the centrifugal force which is developed by impressing rapid rotary motion on the fluid current containing the suspended particles. In particular, the present invention relates to a centrifuge container which is provided with an entrance for the mixed fluid and a superiorly-located exit for the fluid once it has been cleaned of the solid particles. The container is truncoconical, converging towards the bottom thereof, a discharge being located at the bottom of the container which is connected to a collection chamber of the solid particles.

A centrifuge of the above-described type is taught in EP 0 557 251, where the efficiency and performance of the separation are increased by using a centrifuge pump whose impeller, located inside the container above the truncoconical wall, can rotate and accelerate the speed of the water independently of the flow rate and thus achieve a first separation of the particles by centrifuging. The use of a centrifugal pump leads, however, to a certain constructional complexity.

SUMMARY OF THE INVENTION

The main aim of the present invention is to obviate the above-mentioned drawbacks in the prior art by providing a centrifuge separator which is constructionally simple and economical and which at the same time is able to separate a relatively high weight percentage of the solid particles suspended in a fluid, thus providing a high degree of separation.

An advantage of the device is that it provides a very high degree of separation over a broad range of particle dimensions, and is especially efficient in the separation of smaller particles.

A further advantage is that the centrifuge is efficient regardless of the quantity of fluid to be filtered.

A still further advantage is that a high quantity of fluid can be discharged in a short time, even where the fluid flow rate is variable and discontinuous.

Yet further advantages are that the whole unit has no moving parts and is relatively compact.

These aims and advantages and others besides are all achieved by the invention as it is characterised in the accompanying claims.

BRIEF DESCRIPTION OF THE DRAWINGS

Further characteristics and advantages of the present invention will better emerge from the detailed description that follows of a preferred but non-exclusive embodiment of the invention, illustrated purely by way of a non-limiting example in the accompanying figures of the drawings, in which.

DESCRIPTION OF THE PREFERRED EMBODIMENTS

Figure 1:
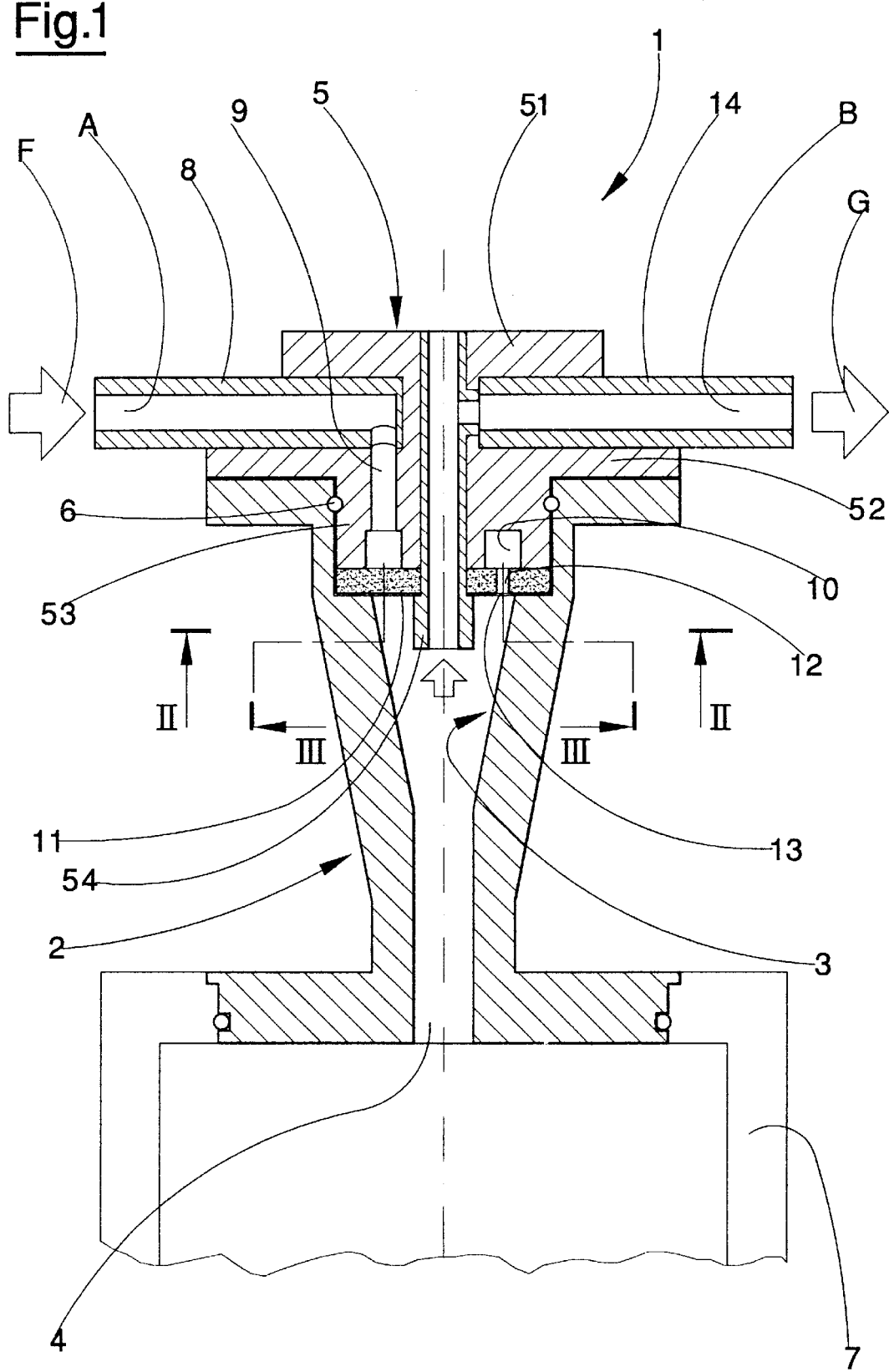
FIG. 1 is a schematic section made according to the vertical line I—I of FIG. 2 of a separator made according to the invention.

With reference to the figures of the drawings, 1 denotes in its entirety a centrifuge separator for separating particles suspended in a fluid.

The separator 1 can especially be used for the separation of solid particles suspended in discharge fluids coming from dental plants, of known type and not illustrated, which produce fluids containing air, water, blood, dental amalgam, chemical products etc., which must be disposed of according to environmental laws which provide for the disposal of substances such as dental amalgam and the like under the definition of special refuse, i.e. refuse which must not be sent into the municipal sewage system. In the case in hand, for example, where the dental equipment uses a wet ring suction pump to aspirate fluids from the patient's mouth, the production of polluting fluids is quite abundant, even if discontinuous. The separator has the task of ridding these fluids of the polluting solid particles before sending the liquids on to the sewers.

The separator 1 comprises a container 2 connected to an inlet A of the fluid containing the particles, and an outlet B, located superiorly in the container, for discharging the fluid rid of the solid particles. The container 2, which can be made of plastic, is provided with a truncoconical (or, truncated conical) wall 3 converging downwards, with a discharge 4 at the bottom thereof. The discharge 4 communicates with a collection chamber 7 located there-below in which the separated solid particles can be accumulated. Means of known type can be provided for almost completely killing turbulence in the fluids entering the chamber 7, also preventing any particles of solid materials from being drawn upwards back into the container 2.

The container 2 is superiorly closed by a lid 5, which can be made of plastic and which is removably coupled to the container 2, for example by means of fastening screws. The container 2 and lid 5 mounted theron make up a separation chamber. In the illustrated example both the inlet A and the outlet B are associated to the lid 5.

The lid 5 laterally exhibits a first mouth 8 bearing the inlet A for receiving the discharge fluid coming from the dental plant in the direction indicated by arrow F. In the example the first mouth 8 is constituted by a cylindrical pipe having a horizontal axis which is made solid to the lid 5. An end of the pipe, comprising the inlet A and laterally projecting from the lid 5, is connectable to means for supplying the discharge fluid containing the solid particles to be separated; the opposite end of the pipe is sunk into the material of which the lid 5 is made, and communicates, though a vertical-axis conduit 9 fashioned in the lid 5 itself, with an underlying annular chamber 10, isolated from the ambient and also fashioned in the lid 5. The chamber 10 is separated from the internal cavity of the container 2 by means of a lower wall 11 of the lid 5 which superiorly delimits the cavity. The lower wall 11 of the lid 5 is located in proximity of the truncoconical wall 3 of the container.

The chamber 10 fashioned in the lid 5 communicates with the inside of the container, in particular with the truncoconical zone thereof, through a plurality of holes 12 made in the body of the lower wall 11 of the lid 5. The holes 12 are straight, for the sake of simplicity, and exhibit an oblique axis directed at least partially tangentially and partly axially with respect to the vertical axis of the truncoconical wall 3. The holes 12 are preferably from three to five in number, are identical and are disposed circumferentially about the axis of the truncoconical wall 3, all at the same height and angularly equidistanced. The number of holes 12 is variable and depends on the size of the separator 1.

The lower outlet of the holes 12 is located very close to the truncoconical wall 3. The lower outlet of the holes 12 is located very close to the truncoconical wall 3. The outlet of each hole 12 is a small mouth 13 through which the container 2 can receive the fluid arriving from inlet A. The container 2 can receive the fluid only through the above-mentioned small mouths 13. The special structure of the above-described lid 5 has substantially the aim of separating the total delivery of fluid reaching the main inlet A into a plurality of smaller jets which are injected tangentially in the truncoconical zone of the container 2. In other words, the container 2 in which the separation is done is supplied with fluid through a plurality of mouths 13, each of which is crossed by a fraction of the total delivery of fluid entering the container 2.

Figure 2:
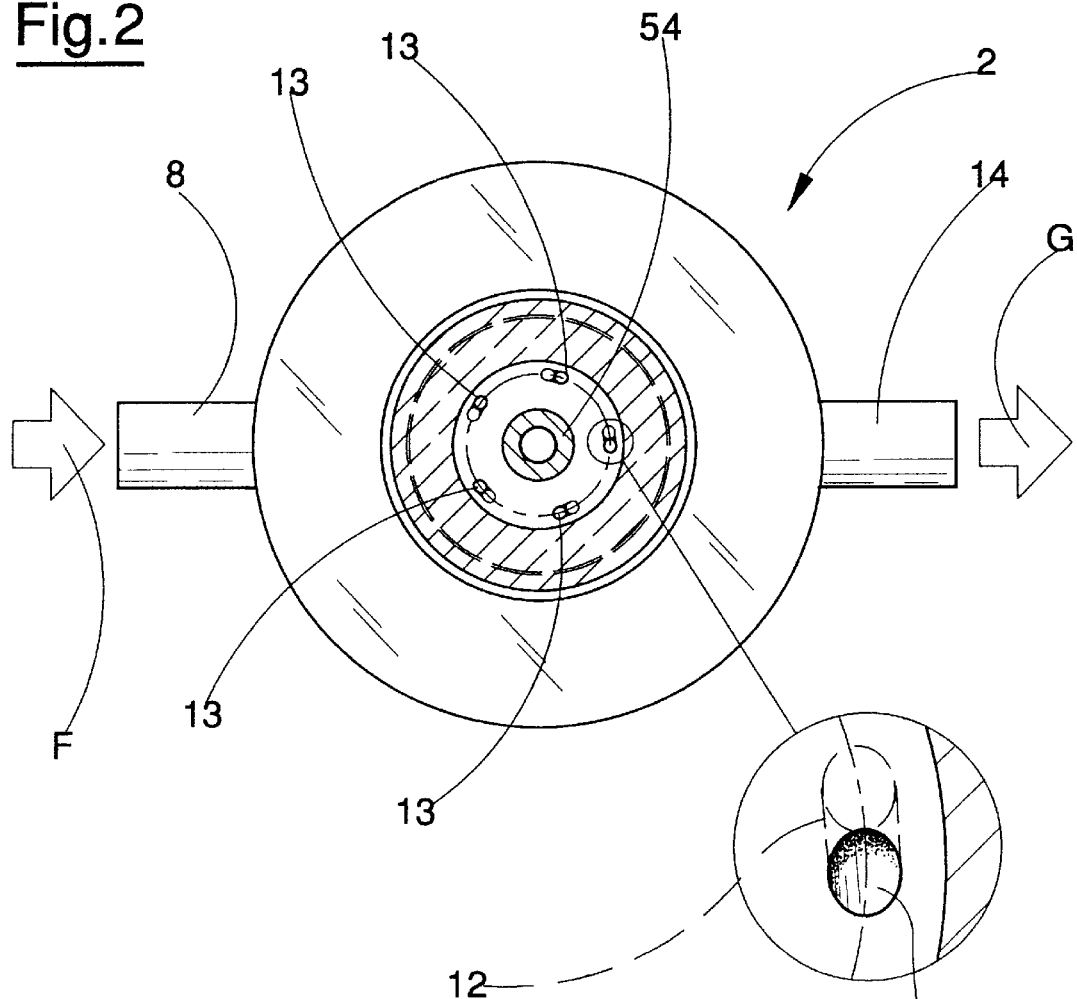
FIG. 2 is a section made according to the horizontal line II—II of FIG. 1.
Figure 3:
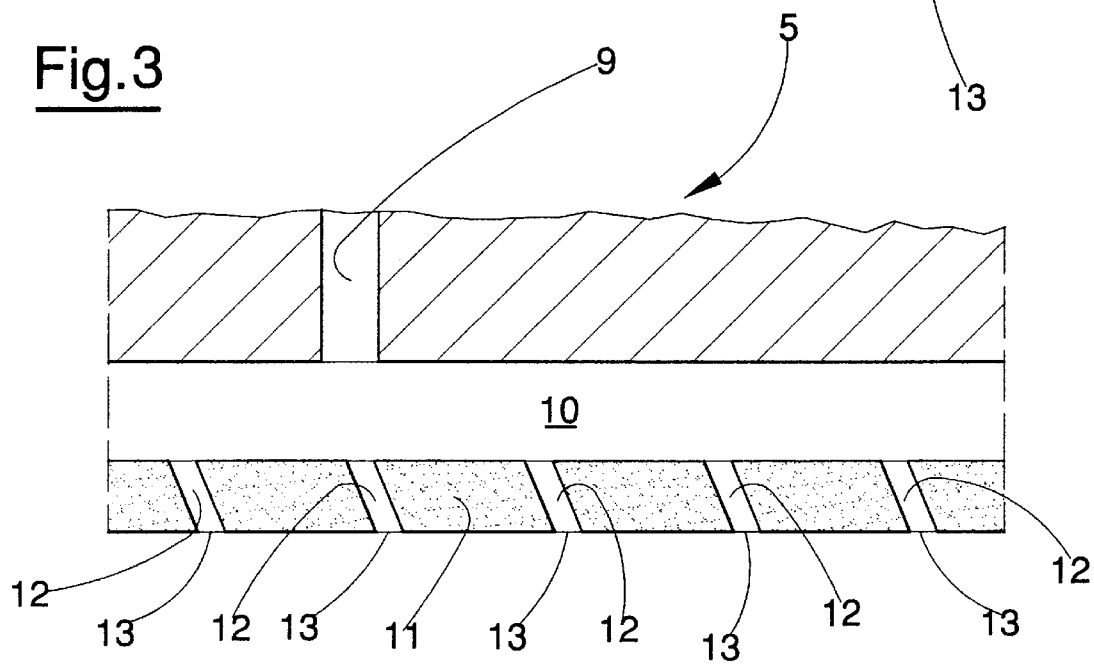
FIG. 3 is a plan view of a section made according to the vertical-axis straight circular cylinder of line III—III of FIG. 1.

Each mouth 13 is located at the end of a conduit (a hole 12) afforded in the lid 5 which at one end opens into the annular chamber 10, and at the other end opens into the container 2 according to an axis whose direction exhibits at least one tangential component and one axial component with respect to the axis of the truncoconical wall 3 that is the conduit axes are skew to the wall axis. In this way the various jets are tangential in order to favour the creation of a centrifugal swirl. The shape of the various conduits (or holes 12) injecting the fluid is clearly represented in FIG. 3, where it can be seen that the axis of the conduits has a tangential component. FIG. 2 shows clearly that the various inlet mouths 13 in the container 2 are equidistant and arranged circumferentially about a vertical axis which coincides with the axis of the truncoconical wall 3.

In the case in point the volume of the inletting fluid is subdivided among five identical mouths 13. Experiments have shown that the effectiveness of separation achieved by the centrifuge is best when the total volume of fluid is fractioned into at least three parts, preferably but not necessarily equal.

In this case the mouths 13 are situated on a wall 11 which superiorly closes the container 2. The mouths 13 can also be laterally arranged, even if for a good separation performance they should be located in the high part of the truncoconical zone of the container.

Each mouth 13 exhibits a passage section which is larger than the largest particle to be separated, thus avoiding risks of blockage in the separator 1. Preferably the passage section of the main mouth 8 of the inlet A, through which the total volume of the fluid passes, should not be smaller (but indeed bigger) than the sum of the passage sections of the single mouths 13.

In the example the lid 5 is made in one piece comprising the following: a cylindrical upper first part 51; a flanged intermediate second part 52 bearing means of known type (not illustrated) for removably coupling with a corresponding flanged part of the underlying container 2; a cylindrical third part 53 located below the second flanged part 52 for inserting (and removing) in a corresponding cavity laterally delimited by a cylindrical wall of the container 2 located immediately above the truncoconical wall 3. Between the cylindrical third part 53 and the container 2 cylindrical wall are situated means for sealing, which in the example is a ring seal 6. The lid 5 further exhibits a vertical-axis tubular body 54 which projects inferiorly, an internal cavity of which is crossed ascendingly by the fluid, which, by now free of the heavier particles, exits from the container 2.

The upper outlet B of the container 2, which is crossed in direction G by the fluid already cleaned of heavy and polluting particles, is usually directed to the sewage system. In the example outlet B is constituted by a second mouth 14 in communication with the inside of the container 2 through a discharge pipe which is partially sunk in the lid 5 material. The discharge pipe is connected to a vertical-axis cylindrical cavity 15 which is centrally-disposed inside the lid 5 and coaxial to the tubular body 54 which projects downwards internally of the container 2. The cavity in the tubular body 54 and the above-mentioned cylindrical cavity 15 are in fact continuous and together form a single outlet conduit internal of the lid 5, coaxial and situated above with respect to the truncoconical wall 3, made solid with the lid 5 and projecting internally of the container 2. The discharge pipe exhibits a lower end which is axially arranged with respect to the truncoconical zone and which is situated in proximity of the larger base thereof, and an opposite end which is connected to outlet B.

The separator 1 can comprise a separator chamber, of known type and not illustrated, arranged upstream of inlet A of the container 2. The separator chamber receives the fluids produced by the dental equipment. Inside the chamber, the gassy part of the fluid is separated from the remainder of the fluid and exits upwards. The remaining part of the fluid collects in the chamber and is sent on to inlet A of the container 2. The function of the separator chamber is mainly to create a water head and maintain the level thereof The separator chamber can be detached from the container 2 or can be in a single-body unit there-with or with the other parts of the separator 1.

Inlet A is connected with the separator chamber and can freely receive the fluid there-from. However, the fluid passage from the chamber to the container is preferably forced by means of pumps (not illustrated).

The separator 1 operates as described herein below.

The fluid, constituted by air, liquids and solid particles, coming from the dental plant, enters the separator chamber; the air, and all other gassy parts, are separated and exit from the top part of the chamber, while the liquid part with the suspended solid particles descends towards the lower part of the chamber and freely passes into the main inlet A of the container 2. The total volume of the fluid passing through the main inlet A is subdivided into several jets which issue tangentially from the various mouths 13 located above the truncoconical zone of the container 2. These jets create a centrifugal swirl which causes separation of the solid particles, which are thrust towards the internal walls of the container 2 and, descending the walls, are directed to the collection chamber 7. The fluid, now free of the heavy solid particles, exits from the top of the container 2 through outlet B, thanks to the creation of an ascending motion in the central zone of the centrifuge. Once the collection chamber 7 contains a predetermined quantity of solid particles, the chamber 7 can be detached and emptied.

The separator of the invention needs only light maintenance, can discharge variable quantities of fluids quickly and gives a good separation performance, even where small particles are concerned, working through a broad range of flow rates of the fluid to be discharged. Further, the separator is advantageously simply and economical to build, and has no moving parts.

What is claimed:

1. A centrifugal separator for separating solid particles suspended in a liquid and collecting the particles in a collection chamber; the separator comprising:
   a separation cavity including
      a truncated conical wall converging in a downward direction to a particle discharge at a small end of the conical wall and
      a static wall mounted statically at a large upper end of the conical wall to superiorly close the separation cavity;
   the static wall comprising a plurality of conduits therethrough connecting the closed space to respective mouths on a lower side of the static wall, the mouths facing downward into the separation cavity;
   the conduits having conduit axes angled obliquely to an axis of the conical wall, whereby the liquid and solid particles are injected into the separation chamber with an axial velocity component and a tangential velocity component;
   an inlet for the liquid and solid particles to enter the conduits; and
   an outlet for the liquid freed of the solid particles, the outlet being situated at a superior point in the separation chamber;
   wherein the particle discharge is adapted for coupling to the collection chamber.

2. The separator of claim 1, wherein the plurality of mouths are at least three in number.

3. The separator of claim 2, wherein said plurality of mouths are circumferentially arranged about the axis of the truncoconical wall.

4. The separator of claim 1, wherein each of said plurality of mouths exhibits a passage section a size of which is greater than a size of a largest solid particle to be separated.

5. The separator of claim 1, wherein said plurality of mouths are connected with a main inlet mouth through which total volume of fluid can be channelled, a passage section of said main inlet mouth being not smaller than a sum of passage sections of all of said plurality of mouths.

6. The separator of claim 5, wherein each of said plurality of mouths is located at an end of one each of a plurality of conduits; another end of which plurality of conduits opens into an annular chamber, which annular chamber is connected to the main inlet mouth.

7. The separator of claim 6, wherein said plurality of conduits and said annular chamber are disposed inside a lid removably associated with the separation cavity, the main inlet mount being integral with the lid; there being also a cylindrical cavity, coaxial to the conical wall and integral with the lid and projecting in a downwards direction from the lid into the separation cavity.

8. The separator of claim 1, wherein the mouths are angularly equidistanced about the axis of the conical wall.

9. The separator of claim 1, wherein the conduits are straight.

10. The separator of claim 1, wherein the conduit directions are skew with respect to the axis of the conical wall.

* * * * *